(12) United States Patent
Zhang et al.

(10) Patent No.: US 12,318,257 B2
(45) Date of Patent: Jun. 3, 2025

(54) SKIN RETRACTION SYSTEM AND SKIN RETRACTOR THEREFOR

(71) Applicant: ZENGZHOU ONE MILLIMETER MEDICAL TECHNOLOGY CO., LTD., Zhengzhou (CN)

(72) Inventors: Mingli Zhang, Zhengzhou (CN); Songlin Li, Zhengzhou (CN); Shuqiang Xie, Zhengzhou (CN); Lanjin Xu, Zhengzhou (CN)

(73) Assignee: ZHENGZHOU ONE MILLIMETER MEDICAL TECHNOLOGY CO., LTD., Henan (CN)

( * ) Notice: Subject to any disclaimer, the term of this patent is extended or adjusted under 35 U.S.C. 154(b) by 622 days.

(21) Appl. No.: 17/625,566

(22) PCT Filed: Jun. 16, 2020

(86) PCT No.: PCT/CN2020/096417
§ 371 (c)(1),
(2) Date: Jan. 7, 2022

(87) PCT Pub. No.: WO2021/008288
PCT Pub. Date: Jan. 21, 2021

(65) Prior Publication Data
US 2022/0287790 A1     Sep. 15, 2022

(30) Foreign Application Priority Data
Jul. 17, 2019   (CN) .......................... 201910645302.7

(51) Int. Cl.
*A61B 90/00*   (2016.01)
*A61B 17/00*   (2006.01)
*A61B 17/08*   (2006.01)

(52) U.S. Cl.
CPC .............. *A61B 90/02* (2016.02); *A61B 17/00* (2013.01); *A61B 2017/00747* (2013.01); *A61B 2017/081* (2013.01)

(58) Field of Classification Search
CPC .............. A61B 17/08; A61B 2017/081; A61B 2017/086; A61B 17/58; A61B 17/60; A61B 2017/606; A61B 17/02–0293
(Continued)

(56) References Cited

U.S. PATENT DOCUMENTS

| | | | |
|---|---|---|---|
| 3,650,274 A | 3/1972 | Edwards et al. | |
| 4,832,026 A * | 5/1989 | Jones ................. | A61B 17/0643 606/216 |

(Continued)

FOREIGN PATENT DOCUMENTS

| | | |
|---|---|---|
| CN | 102198010 A | 9/2011 |
| CN | 205744882 U | 11/2016 |

(Continued)

OTHER PUBLICATIONS

International Search Report for PCT Application No. PCT/CN2020/096417; China National Intellectual Property Administration; Beijing, China; date of mailing Aug. 28, 2020.
(Continued)

*Primary Examiner* — Kathleen S Holwerda
*Assistant Examiner* — Serenity A Miller
(74) *Attorney, Agent, or Firm* — Thomas E. Lees, LLC

(57) ABSTRACT

This disclosure relates to a skin traction system and a skin retractor thereof. When the skin retractor of this disclosure is in use, a winding roller is rotated to wind a bracing wire on the winding roller, the winding roller is in a lock position, the locking is achieved through the matching of a scotch structure and a matching structure, thereby preventing the winding roller from rolling back; when it is necessary to
(Continued)

loosen the bracing wire, push the winding roller along the winding roller to move it from the lock position to the unlock position, so that the scotch structure and the matching structure disengage, and the winding roller is in a free state, the bracing wire is loosened and detached from the winding roller under the opposite acting force, thereby realizing the loosening of the bracing wire.

7 Claims, 4 Drawing Sheets

(58) Field of Classification Search
USPC .................................. 606/215–218, 232, 233
See application file for complete search history.

(56) References Cited

U.S. PATENT DOCUMENTS

| | | | | |
|---|---|---|---|---|
| 5,522,827 | A | * | 6/1996 | Combs ............. A61B 17/32056 606/167 |
| 2003/0225436 | A1 | | 12/2003 | Fleischmann |
| 2013/0079821 | A1 | | 3/2013 | Hahn |

FOREIGN PATENT DOCUMENTS

| | | |
|---|---|---|
| CN | 107714191 A | 2/2018 |
| CN | 109480942 A | 3/2019 |
| CN | 208725774 U | 4/2019 |
| CN | 110432994 A | 11/2019 |
| RU | 2236185 C2 | 9/2004 |
| WO | 2009118487 A1 | 10/2009 |

OTHER PUBLICATIONS

Written Opinion of the International Searching Authority for PCT Application No. PCT/CN2020/096417; China National Intellectual Property Administration; Beijing, China; date of mailing Aug. 28, 2020.

Extended European Search Report for European Application No. 20840130.7; European Patent Office, Munich Germany; dated Jul. 17, 2023.

First Office Action for Russian Application No. 202290257; Eurasian Patent Office, Moscow Russia; dated Sep. 29, 2022.

First Office Action for Chinese Application No. 201910645302.7; China National Intellectual Property Administration; Beijing, China; dated May 18, 2024.

* cited by examiner

SKIN RETRACTION SYSTEM AND SKIN RETRACTOR THEREFOR

CROSS-REFERENCE TO RELATED APPLICATIONS

This application is a national stage entry under 35 USC § 371 (b) of PCT International Application No. PCT/CN2020/096417, filed on Jun. 16, 2020, and claims the benefit of Chinese Patent No. 201910645302.7, filed on Jul. 17, 2019, which are expressly incorporated by reference herein.

BACKGROUND

This disclosure relates to a skin retraction system and a skin retractor thereof.

When skin tissue is damaged, special medical equipment is needed to stretch the skin so that the damaged skin can grow under the action of tension until the wound is healed. A skin retractor is a device that can achieve this function. For example, the Chinese patent document under the publication number of application CN109480942A discloses a skin retractor, which pierces two steel needles through the skin on both sides of a wound, and at the same time, a bracing wire is wound around the two steel needles to apply a pulling force to the two steel needles, the free end of the bracing wire is wound on a winding roller of the retractor, the length of the bracing wire wound on the winding roller is adjusted by rotating the winding roller, thereby adjusting the pulling force of the bracing wire; the volume of the bracing wire is quite small, which is convenient for overlapping and crossing, thus avoiding accidental touch by the patient during use, and the safety is high. Besides, the use of a bracing wire is also convenient for traction of atypical wounds. The locking mechanism of the winding roller of this type of retractor specifically adopts a locking sleeve and a tetragonal structure on the winding roller to achieve locking. When in use, it is necessary not only to operate the winding roller but also to operate the locking sleeve at the same time to achieve the locking between the two, so the operation is inconvenient.

BRIEF SUMMARY

This disclosure provides a skin retractor to solve the technical problem of inconvenient operation of the existing skin retractor; at the same time, this disclosure also provides a skin traction system using the skin retractor.

The skin retractor of this disclosure adopts the following technical solutions:

The skin retractor includes a retractor body before installation that extends in the up and down direction, a jacking piece disposed in the installation cavity, and an elastic member for providing elastic force to the jacking piece. The retractor body is rotatably equipped with a winding roller for winding a corresponding bracing wire. The jacking piece has a cable channel connected with the installation cavity for the corresponding bracing wire to pass through. The winding roller is connected with a locking mechanism for locking it. The locking mechanism includes a scotch structure provided on the winding roller and a matching structure capable of matching with the scotch structure and provided on the retractor body. The winding roller matches with the retractor body for guided movement along its axial direction, having a lock position where the scotch structure and the matching structure match, and an unlock position where the scotch structure and the matching structure disengage.

The winding roller is connected with a locking elastic member for keeping it in the lock position.

One end of the winding roller is cantilevered to the outside of the retractor body and is installed with an operating sleeve. The locking elastic member is sleeved on the winding roller and is located in the inner cavity of the operating sleeve.

The retractor body is provided with a guide structure that guides the winding roller to move between the lock position and the unlock position along its axial direction.

The guide structure is a guide sleeve sleeved on the winding roller. One end of the guide sleeve penetrates into the inner cavity of the operating sleeve, and the other end is jacked against the retractor body. The locking elastic member is a cylindrical spring jacked between the guide sleeve and the operating sleeve.

The winding roller is provided with a washer installed at one end of the cylindrical spring facing away from the guide sleeve.

The scotch structure is a prismatic structure provided on the winding roller, and the matching structure is a matching groove provided on the retractor body to match with the prismatic structure.

The prismatic structure is a hexagonal structure.

The skin traction system of this disclosure adopts the following technical solutions:

The skin traction system includes a skin retractor and two steel needles for piercing through the skin on both sides of a wound. A bracing wire is threaded between the two steel needles. The skin retractor includes a retractor body before installation that extends in the up and down direction, a jacking piece disposed in the installation cavity, and an elastic member for providing elastic force to the jacking piece. The retractor body is rotatably equipped with a winding roller for winding a corresponding bracing wire. The jacking piece has a cable channel connected with the installation cavity for the corresponding bracing wire to pass through. The winding roller is connected with a locking mechanism for locking it. The locking mechanism includes a scotch structure provided on the winding roller and a matching structure capable of matching with the scotch structure and provided on the retractor body. The winding roller matches with the retractor body for guided movement along its axial direction, having a lock position where the scotch structure and the matching structure match, and an unlock position where the scotch structure and the matching structure disengage.

The winding roller is connected with a locking elastic member for keeping it in the lock position.

One end of the winding roller is cantilevered to the outside of the retractor body and is installed with an operating sleeve. The locking elastic member is sleeved on the winding roller and is located in the inner cavity of the operating sleeve.

The retractor body is provided with a guide structure that guides the winding roller to move between the lock position and the unlock position along its axial direction.

The guide structure is a guide sleeve sleeved on the winding roller. One end of the guide sleeve penetrates into the inner cavity of the operating sleeve, and the other end is jacked against the retractor body. The locking elastic member is a cylindrical spring jacked between the guide sleeve and the operating sleeve.

The winding roller is provided with a washer installed at one end of the cylindrical spring facing away from the guide sleeve.

The scotch structure is a prismatic structure provided on the winding roller, and the matching structure is a matching groove provided on the retractor body to match with the prismatic structure.

The prismatic structure is a hexagonal structure.

The beneficial effects of this disclosure are: when the skin retractor of this disclosure is in use, a winding roller is rotated to wind a bracing wire on the winding roller, the winding roller is in a lock position, the locking is achieved through the matching of a scotch structure and a matching structure, thereby preventing the winding roller from rolling back. When it is necessary to loosen the bracing wire, push the winding roller along the winding roller to move it from the lock position to the unlock position, so that the scotch structure and the matching structure disengage, and the winding roller is in a free state, the bracing wire is loosened and detached from the winding roller under the opposite acting force, thereby realizing the loosening of the bracing wire. The skin retractor of this disclosure needs only to move the winding roller axially when unlocking and locking, without having to operate other parts, so the operation is convenient during use.

BRIEF DESCRIPTION OF THE DRAWINGS

In order to explain the embodiments of this disclosure or the technical solutions in the prior art more clearly, the following will briefly introduce the drawings that need to be used in the embodiments or the prior art. Obviously, the drawings in the following description are only some embodiments of this disclosure. Those having ordinary skill in the art can obtain other drawings based on these drawings without creative effort involved.

In the figures: 1. Operating sleeve; 2. Washer; 3. Winding roller; 4. Locking elastic member; 5. Guide sleeve; 6. Fixation sleeve; 7. Elastic member washer; 8. Fixation tube; 9. Elastic member; 10. Piston cone; 31. Scotch structure; 61. Matching structure; 11. Operating sleeve cavity; 12. Threaded hole; 13. Step surface; 14. Plane; 32. Threaded section.

DETAILED DESCRIPTION OF THE DISCLOSURE

The technical solutions in the embodiments of this disclosure will be clearly and completely described below in conjunction with the accompanying drawings in the embodiments of this disclosure. Obviously, the described embodiments are only a part of, rather than all, the embodiments of this disclosure. All other embodiments obtained by those having ordinary skill in the art based on the embodiments in this disclosure without contributing any creative effort shall fall within the protection scope of this disclosure.

Figure 1:
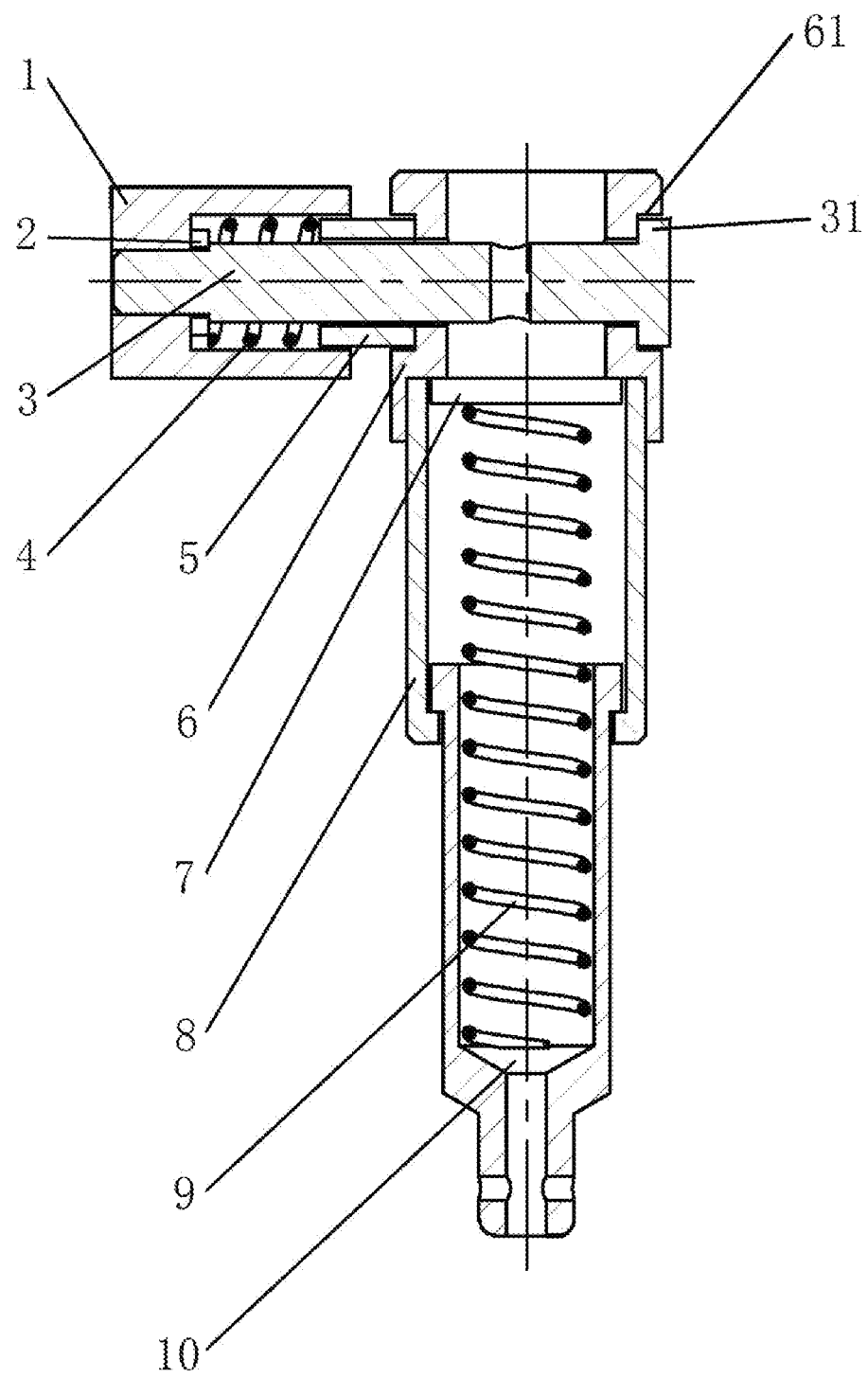
FIG. 1 is a schematic diagram of the structure of a skin retractor in the embodiment of the skin traction system of this disclosure.
Figure 2:
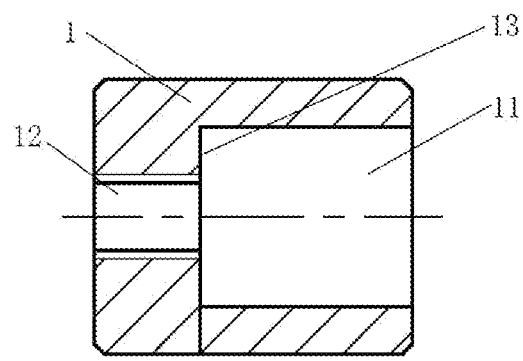
FIG. 2 is a schematic diagram of the structure of the operating sleeve in FIG. 1.
Figure 3:
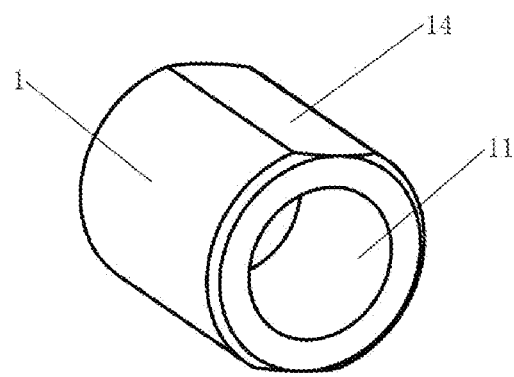
FIG. 3 is a graphic model of FIG. 2.
Figure 4:
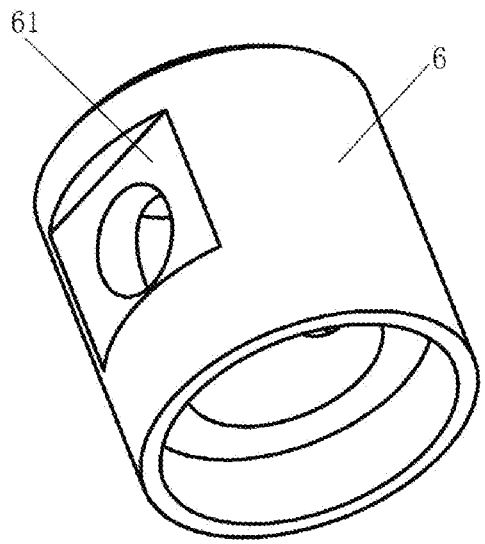
FIG. 4 is a schematic diagram of the structure of a fixation sleeve.
Figure 5:
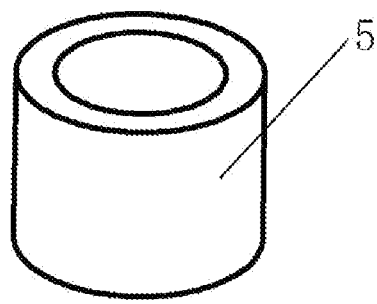
FIG. 5 is a schematic diagram of the structure of a guide sleeve.
Figure 6:
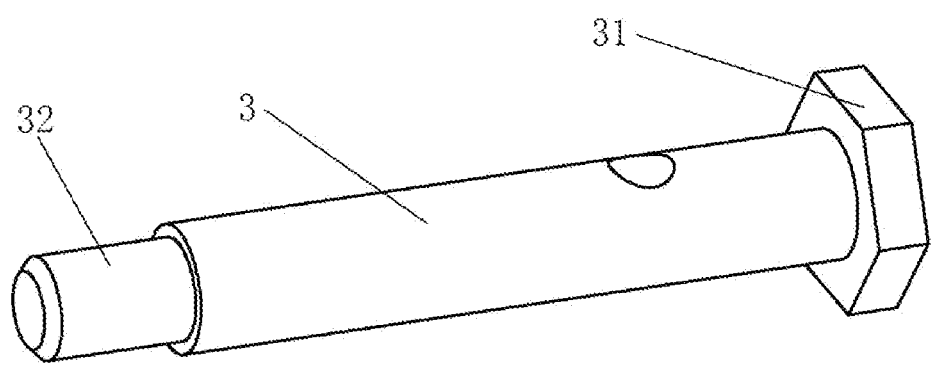
FIG. 6 is a schematic diagram of the structure of a winding roller.

The embodiment of the skin traction system of this disclosure is shown in FIGS. 1 to 6. The skin traction system includes a skin retractor and two steel needles for piercing through the skin on both sides of a wound. A bracing wire is threaded between the two steel needles. The skin retractor includes a retractor body before installation that extends in the up and down direction, a jacking piece disposed in the installation cavity, and an elastic member 9 for providing elastic force to the jacking piece. The elastic member 9 is a cylindrical spring. The retractor body is rotatably equipped with a winding roller 3 for winding a corresponding bracing wire. The jacking piece has a cable channel connected with the installation cavity for the corresponding bracing wire to pass through. The winding roller 3 is connected with a locking mechanism for locking it. The locking mechanism includes a scotch structure 31 provided on the winding roller 3 and a matching structure 61 capable of matching with the scotch structure 31 and provided on the retractor body. The winding roller 3 matches with the retractor body for guided movement along its axial direction, having a lock position where the scotch structure 31 and the matching structure 61 match, and an unlock position where the scotch structure 31 and the matching structure 61 disengage.

In this embodiment, the retractor body has a split structure, including a fixation sleeve 6 and a fixation tube 8, which are in an interference fit.

In this embodiment, the winding roller 3 is connected with a locking elastic member 4 that keeps it in the lock position, thus can keep the winding roller 3 in the lock position, thereby preventing the winding roller 3 from accidentally loosening.

In order to facilitate the operation of the winding roller, in this embodiment, one end of the winding roller is cantilevered to the outside of the retractor body and is installed with an operating sleeve 1. The locking elastic member 4 is sleeved on the winding roller and is located in the inner cavity of the operating sleeve 1. In this embodiment, the operating sleeve 1 and the winding roller are detachably connected through a threaded structure, which facilitates later assembly. The inner cavity of the operating sleeve 1 is a stepped hole structure, the threaded hole 12 at the rear end is used for threading fit with the winding roller, and the stepped surface 13 is used for positioning. Around the operating sleeve 1 is provided with a plane 14, making it a flat structure, which is convenient for performing the rotating operation thereto.

In this embodiment, in order to facilitate the circumferential movement of the winding roller, a guide structure is provided on the retractor body to guide the winding roller to move between the lock position and the unlock position along its axial direction. To be specific, the guide structure is a guide sleeve 5 sleeved on the winding roller. One end of the guide sleeve 5 penetrates into the inner cavity of the operating sleeve 1, and the other end is jacked against the retractor body. The locking elastic member 4 is a cylindrical spring jacked between the guide sleeve 5 and the operating sleeve 1. The winding roller is provided with a washer 2 installed at one end of the cylindrical spring facing away from the guide sleeve 5. The washer 2 can stop and limit the operating sleeve 1.

During the specific traction, it is first necessary to press the operating sleeve 1 so that the operating sleeve drives the winding roller to move axially against the elastic force of the cylindrical spring, the operating sleeve and the winding roller at this time both move relative to the guide sleeve, and the scotch structure 31 disengages from the matching structure 61, then rotate the winding roller by the operating sleeve to wind the bracing wire on the winding roller. After the winding is in place, reduce the force on the axial direction of the operating sleeve. At this time, the elastic force of the cylindrical spring makes the winding roller reset to stop rotation and be in a locked state.

In order to reduce the processing complexity of the scotch structure 31, in this embodiment, the scotch structure 31 is a prismatic structure provided on the winding roller, and the matching structure 61 is a matching groove provided on the retractor body to match with the prismatic structure. To be specific, the prismatic structure is a hexagonal structure, which is convenient to control the locking angle of the winding roller, thereby providing a more precise pulling force. A section of the winding roller is provided with a threaded section for matching with the threaded hole to realize the detachable connection between the two.

When the skin retractor of this disclosure is in use, the winding roller is rotated to wind the bracing wire on the winding roller, the winding roller is in a lock position, the locking is achieved through the matching of the scotch structure and the matching structure, thereby prevent the winding roller from rolling back. When it is necessary to loosen the wire, push the winding roller along the winding roller to move it from the lock position to the unlock position, so that the scotch structure and the matching structure disengage, and the winding roller is in a free state, the bracing wire is loosened and detached from the winding roller under the opposite acting force, thereby realizing the loosening of the bracing wire. The skin retractor of this disclosure needs only to move the winding roller axially when unlocking and locking, without having to operate other parts, so the operation is convenient during use.

In other embodiments of this disclosure, the locking elastic member can also be a butterfly spring; the position of the locking elastic member can also be arranged between the scotch structure and the fixation sleeve; the guide structure can also be integrally arranged with the fixation sleeve; the scotch structure can further be a locking pin provided on the winding roller, the locking pin extends along the radial direction of the winding roller, and the fixation sleeve is provided with slots for the locking pin to match, the number of the slots can be plural; the prismatic structure can also be a quadrangular structure, or can also be an elliptical structure; the scotch structure can also be a serrated structure.

In an embodiment of the skin retractor of this disclosure, the skin retractor has a structure same as that of the skin retractor in the embodiment of the above skin traction system, and will not be repeated.

The above are only the preferred embodiments of this disclosure and are not intended to limit this disclosure. Any modification, equivalent replacement, improvement and the like made within the spirit and principle of this disclosure shall fall within the protection scope of this disclosure.

The invention claimed is:

1. A skin retractor, including a retractor body before installation that extends in an up and down direction, a jacking piece disposed in an installation cavity, and an elastic member for providing an elastic force to the jacking piece, the retractor body being rotatably equipped with a winding roller for winding a corresponding bracing wire, the jacking piece having a cable channel connected with the installation cavity for the corresponding bracing wire to pass through, the winding roller being connected with a locking mechanism for locking it, characterized in that the locking mechanism includes a scotch structure provided on the winding roller and a matching structure capable of matching with the scotch structure and provided on the retractor body, wherein the scotch structure is a prismatic structure, a locking pin, or a serrated structure provided on the winding roller, the winding roller matches with the retractor body for a guided movement along its axial direction, having a lock position where the scotch structure and the matching structure match, and an unlock position where the scotch structure and the matching structure disengage, the winding roller is connected with a locking elastic member for keeping it in the lock position, and one end of the winding roller is cantilevered to an outside of the retractor body and is installed with an operating sleeve, the locking elastic member is sleeved on the winding roller and is located in an inner cavity of the operating sleeve.

2. The skin retractor of claim 1, characterized in that the retractor body is provided with a guide structure that guides the winding roller to move between the lock position and the unlock position along its axial direction.

3. The skin retractor of claim 2, characterized in that the guide structure is a guide sleeve sleeved on the winding roller, one end of the guide sleeve penetrates into the inner cavity of the operating sleeve, the other end is jacked against the retractor body, the locking elastic member is a cylindrical spring jacked between the guide sleeve and the operating sleeve.

4. The skin retractor of claim 3, characterized in that the winding roller is provided with a washer installed at one end of the cylindrical spring facing away from the guide sleeve.

5. The skin retractor of claim 1, characterized in that the scotch structure is a prismatic structure provided on the winding roller, and the matching structure is a matching groove provided on the retractor body to match with the prismatic structure.

6. The skin retractor of claim 5, characterized in that the prismatic structure is a hexagonal structure.

7. A skin traction system, including a skin retractor and two steel needles for piercing through the skin on both sides of a wound, and a bracing wire being threaded between the two steel needles, characterized in that: the skin retractor is the skin retractor of claim 1.

* * * * *